United States Patent [19]
Chaplin et al.

[11] Patent Number: 4,654,871
[45] Date of Patent: Mar. 31, 1987

[54] METHOD AND APPARATUS FOR REDUCING REPETITIVE NOISE ENTERING THE EAR

[75] Inventors: George B. B. Chaplin; Roderick A. Smith, both of Colchester; Terrence P. C. Bramer, Ipswich, all of United Kingdom

[73] Assignee: Sound Attenuators Limited, Essex, United Kingdom

[21] Appl. No.: 719,034

[22] PCT Filed: Jun. 11, 1982

[86] PCT No.: PCT/GB82/00176

§ 371 Date: Feb. 9, 1983

§ 102(e) Date: Feb. 9, 1983

[87] PCT Pub. No.: WO82/04479

PCT Pub. Date: Dec. 23, 1982

Related U.S. Application Data

[63] Continuation-in-part of Ser. No. 467,480, Feb. 9, 1983, abandoned.

[30] Foreign Application Priority Data

Jun. 12, 1981 [GB] United Kingdom ................ 8118022

[51] Int. Cl.[4] ........................ G01K 11/16; A61F 11/02
[52] U.S. Cl. ........................................ 381/72; 381/94
[58] Field of Search ............................ 381/72, 74, 94; 181/206, 129

[56] References Cited

U.S. PATENT DOCUMENTS 2,972,018 2/1969 Hawley et al. ...................... 381/71

FOREIGN PATENT DOCUMENTS 1530814 11/1978 United Kingdom .
1577322 10/1980 United Kingdom .

*Primary Examiner*—James L. Dwyer
*Attorney, Agent, or Firm*—Dann, Dorfman, Herrell & Skillman

[57] ABSTRACT

Apparatus for improving the audibility of incident sound (4) to a person (3) operating in an environment where there is a substantial background noise field (2) coming from a source (1) of repetitive noise, comprises an adaptable waveform generator (7), a first electro-acoustic transducer (10) receiving a synthesized cancelling waveform from the generator (7) and generating a cancelling noise to at least partly null the background noise, a second electro-acoustic transducer (11) to sense the partially nulled background noise, and adaptor (13) to modify the output of the generator (7) on the basis of the electrical output signal from the second transducer to minimize the nulled background noise, and sensor (5) to feed a triggering signal (6) derived from the source to the waveform generator. The electro-acoustic transducers (10, 11) can be mounted in headset (8) holding the transducers adjacent to an ear of said person without substantially impeding the arrival of said incident sound (4) to said ear.

8 Claims, 5 Drawing Figures

20
ADAPTOR
13''
17
16
WAVEFORM GENERATOR
7''
19
18
SUMMER
6''
5''
1''
NOISE SOURCE
SYNC. PULSE GENERATOR

SYNC
PULSE
GENERATOR
NOISE
1
SOURCE
WAVEFORM
GENERATOR
ADAPTOR
7
2
4
5
6
8
9
10
11
12
13
14
3

SUMMER
FIRST
ADAPTOR
FIRST
WAVEFORM
GENERATOR
SECOND
ADAPTOR
SECOND
WAVEFORM
GENERATOR
FIRST
SYNC. PULSE
GENERATOR.
SECOND
SYNC. PULSE
GENERATOR
FIRST NOISE SOURCE
SECOND NOISE SOURCE.
15
10
11
13
7
2'
13'
7'
6
2
5
5'
6'
1
1'

METHOD AND APPARATUS FOR REDUCING REPETITIVE NOISE ENTERING THE EAR

This is a continuation-in-part patent application of prior application Ser. No. 467,480, filed Feb. 9, 1983, now abandoned.

TECHNICAL FIELD

This invention relates to an improved arrangement for the active cancellation of repetitive noise at the location of the ears of a person operating in an environment where there is at least a substantial background of such noise. The method and apparatus of which this invention relates has the advantage that because the cancellation only affects noise synchronised to the source (or sources) of the background noise, the bulk of the low frequency spectrum which is not synchronised remains unaffected, thus allowing good speech intelligibility, or improved audibility of sounds unsynchronised to the noise source, in the presence of low frequency machinery-induced noise. Thus warnings and sounds not related to the machinery will be substantially unaffected and their audibility can thus be enhanced by the method and apparatus described herein.

BACKGROUND ART

British Patent Specification No. 1577322 discloses a method of reducing the amplitude of sound variations received at a selected location from a source of recurring noise which employs a waveform generator producing a synthesised waveform capable of being used to generate a cancelling sound in the location for the noise entering that location and uses a triggering signal, derived from the source, to accurately relate the generation of the cancelling sound to the noise it is wished to cancel. This prior specification (the entire disclosure of which is herein incorporated by reference) forms the basis for the present invention.

It is also known from Wheeler and Halliday's published representation (entitled "An active noise reduction system for aircrew helmets—flight trials in strike aircraft") presented at Birkbeck College, London, on Feb. 16, 1981, to mount an active noise reduction system in a passive ear defender to cancel the acoustic noise field detected inside an ear defender. However this known arrangement is incapable of distinguishing between components of the noise field and is thus of limited use and is not effective at all for improving the audibility of random signals appearing in a high background of repetitive noise signals.

BRIEF STATEMENTS OF INVENTION

According to one aspect of the present invention there is provided a method for discriminating between a desired signal fed to an ear of a hearer and an interfering background noise in the hearer's ear, derived from a source of repetitive noise signals, which method comprises feeding a cancelling waveform to an acoustic transducer adjacent to the hearer's ear, and adjusting the cancelling waveform to optimise the efficiency of cancellation obtained in the hearer's ear, which method is characterised in that the noise-cancelling waveform is synchronised to the source of repetitive noise to selectively cancel that component of the sound reaching the hearer's ear which is derived from the said source.

In one embodiment, an open-backed headset is employed so that the repetitive background noise and the signal which the hearer wishes to hear are both airborne to the hearer's ear and the background noise is more strongly attenuated than the signal by an acoustic transducer carried in the headset. Normally of course separate acoustic transducers will be provided for each ear and suitably each transducer is fed with its own cancelling waveform derived from a separate waveform generator. The two generators can, however, receive common synchronising trigger signals from the noise source.

In a second embodiment, a closed-back headset is employed, the required signal being fed electrically to an acoustic transducer adjacent to the ear. Some background noise from the source of repetitive noise (particularly the lower frequency components) leaks around the seal between the headset and the wearer's head, but this can be selectively cancelled by feeding the appropriate noise cancelling waveform to the transducer with the required signal.

In a third embodiment, a headset is again employed, but here the noise signal is arriving with the required signal to the acoustic transducer in the headset. Once again an appropriate cancelling waveform synchronised with the noise is fed to the transducer to selectively eliminate the arriving noise signal and permit the hearer to more clearly discern the required non-synchronised signal.

Where there is more than one source of repetitive noise contributing to the background noise, a separate waveform generator can be synchronised respectively to each source, and the outputs from the separate generators can be fed to a common transducer for the or each ear.

According to a further aspect of the invention, apparatus for improving the audibility of incident sound to a person operating in an environment where there is a substantial background noise in the person's ear coming from a source of repetitive noise, comprises an adaptable waveform generator, a first electro-acoustic transducer receiving a synthesised cancelling waveform from the generator and generating a cancelling noise to at least partly null the background noise in the person's ear, a second electro-acoustic transducer to sense that partially nulled background noise, and adaptive means to modify the output of the generator on the basis of the electrical output signal from the second transducer to minimise the nulled background noise, and means to feed a triggering signal derived from the source to the waveform generator, is characterised in that the electro-acoustic transducers are mounted in a means holding the transducers adjacent to an ear of said person without substantially impeding the audibility of said incident sound to said ear.

The head mounting means preferably includes two ear pieces, one for each ear of the wearer, each equipped with said first and second transducers.

The means to feed the triggering signal can be optical, ultra-sonic or electrical (e.g. by wire or inductive loop) and suitably the apparatus is portable by the person (e.g. it can be incorporated in the head-mounting means).

The waveform generator can be of the type described in the aforementioned British Patent Specification No. 1577322.

BRIEF DESCRIPTION OF DRAWINGS

The invention will now be further described, by way of example, with reference to the accompanying drawings, in which.

DESCRIPTION OF SPECIFIC EMBODIMENTS

Figure 1:
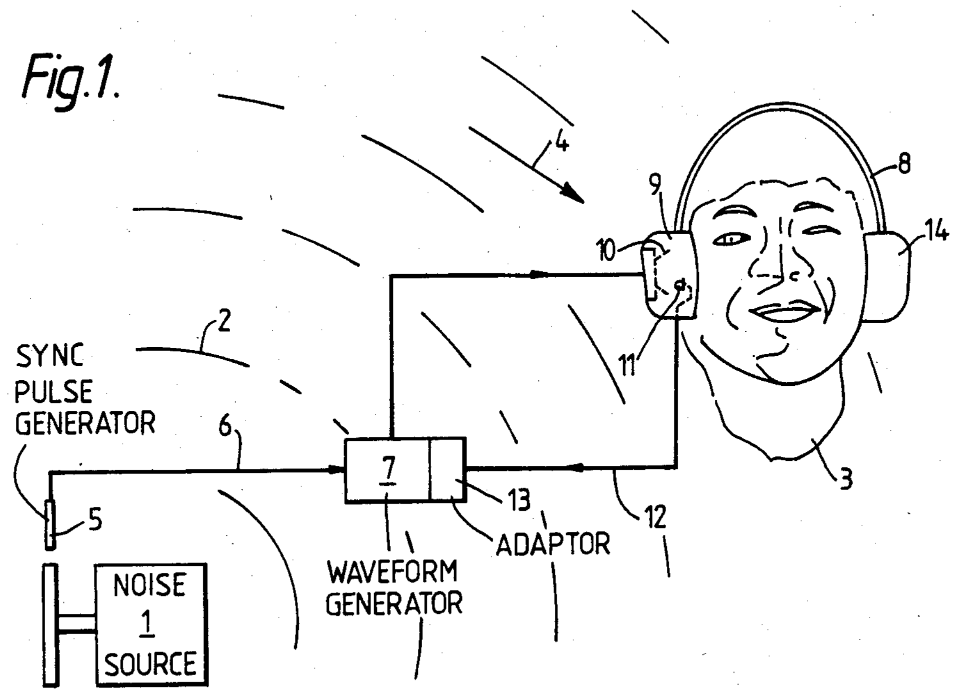
FIG. 1 schematically shows one form of apparatus according to the invention for reducing airborne background noise from a single source of repetitive noise in one ear of a hearer.

Referring to FIG. 1, a source 1 of recurring noise (e.g. an engine) generates a high background noise field 2 in an environment which includes a person 3 wishing to hear an incident sound 4 which is not related to the noise field 2.

A source of synchronising pulses 5 is associated with the source 1 and feeds triggering pulses 6 to an adaptive waveform generator 7. The source 5 can be, for example an electrical transducer associated with a toothed flywheel of an engine, and the pulses 6 can be transmitted by a wire, by an optical (e.g. infra-red) link, ultrasonically or via an inductive loop to the generator 7. The generator 7 can be of the kind described in British Patent Specification No. 1577322.

Figure 5:
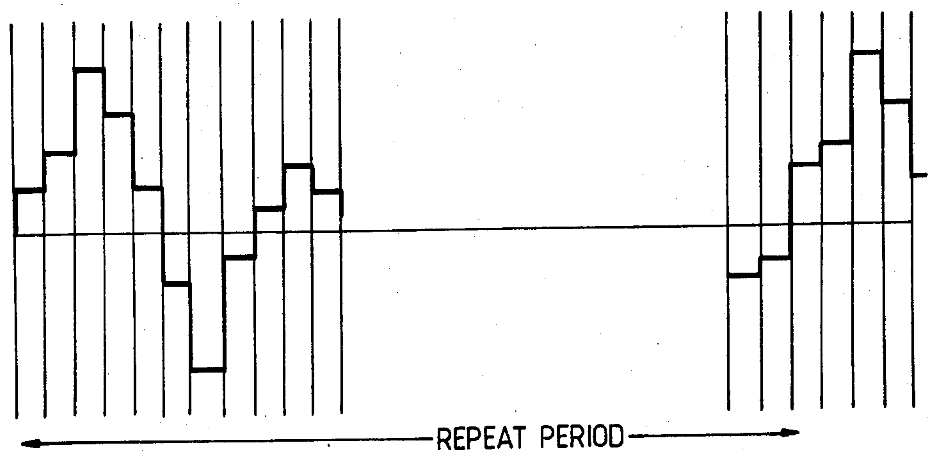
FIG. 5 shows how a cancelling waveform is synthesized with the equipment of FIG. 4.
Figure 4:
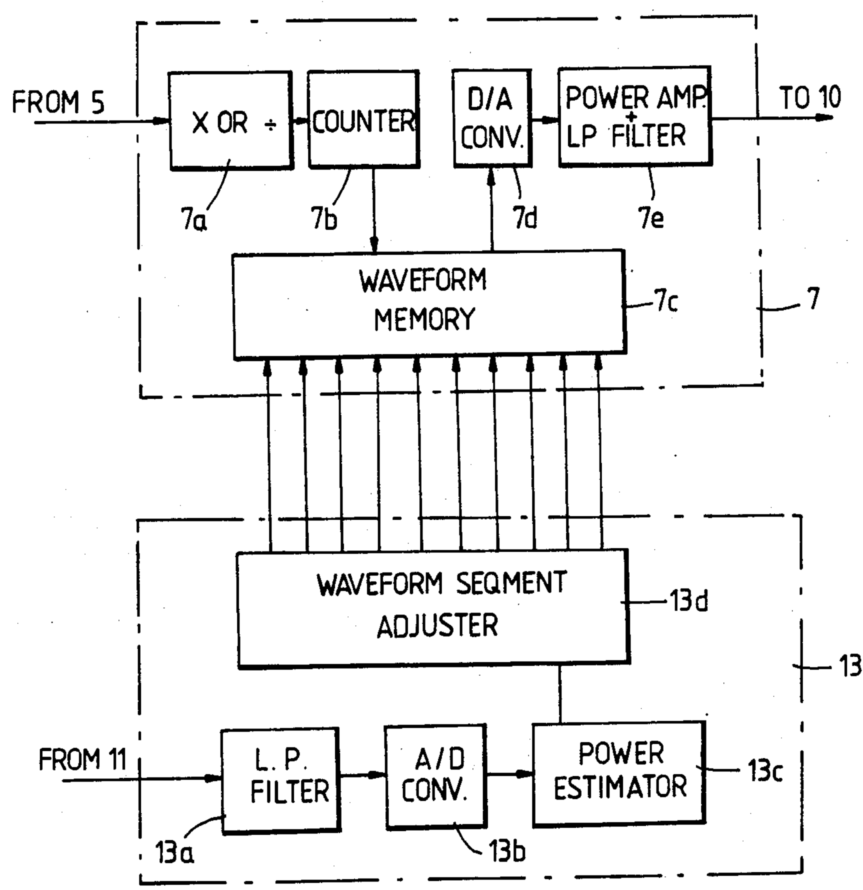

The person 3 wears a head-set 8 having an open earphone 9 over his right ear, which earphone 9 permits both the noise field 2 and the sound 4 to enter through it to the ear covered thereby. Within the earphone 9 is a speaker 10 and a closely adjacent microphone 11. A signal 12 from the microphone 11 is fed back to an adaptive means 13 forming a part of the generator 7. The arrangement of the components 7, 10, 11, 13 is such that the output from the generator 7 is adjusted from time-to-time to ensure that the output from the speaker 10 nulls the noise field 2 in the ear (i.e. the adaption algorithm is programmed to minimise the microphone signal from the vicinity of the earphone cavity). The means for achieving this are clearly described in the aforesaid specification and need only be briefly detailed here. One form of waveform generator 7 and adaptor 13 which can be used by the system of FIG. 1 is illustrated in FIG. 4. The waveform generator synthesises contiguous segments to produce the wave shape shown in FIG. 5. The waveform must maintain a consistent 180° phase relationship with the background noise in order to produce cancellation. This is achieved by triggering the waveform generator 7 from the synchronisation signal pulses 6. Preferably the synchronisation signal is derived from a toothed slotted wheel or the like, driven directly by the source 1 (e.g. an engine). The teeth of slots can be sensed in any convenient way which might be electrical, magnetic or optical, but does not preclude other options.

Ideally, the number of slots or teeth should correspond to n, the desired number of segments in the waveform. In this manner each tooth or slot can be used to trigger a unique segment in the waveform on a sequential basis. If the number of teeth or slots is greater than the number of segments, then the synchronisation signal will require frequency dividing. Conversely, if the number of teeth or slots is less than the number of segments, the synchronisation signal will require frequency multiplying, ideally with a circuit incorporating a phase lock loop so that any frequency modulation by the synchronisation signal is followed by the multiplied signal. The frequency divider/multiplier is shown at 7*a* in FIG. 4 and a counter at 7*b*.

One preferred microprocessor implementation of the waveform triggering is to store each contiguous segment of the waveform in unique but contiguous memory addresses. The synchronisation signal is used to drive a memory addresser, which may be a software incremental counter controlled by interrupts generated from the synchronisation signal in such a way that the waveform memory is addressed sequentially during each repeat cycle. If the synchronisation signal requires division as described above, this can be readily achieved in some instances by inhibiting the count increment. For example, if there are twice as many teeth as required, the counter can be programmed to increment on every other interrupt.

Thus the waveform memory 7*c* shown in FIG. 4 stores a plurality of samples each having a unique address in the memory 7*c*. The samples represent portions of a precursor of the required waveform to be generated and are presented sequentially to a digital-to-analog converter 7*d* (which is followed by a power amplifier and a low pass filter 7*e* to remove sampling frequencies) to generate the actual waveform to be fed to the transducer 10. As explained, it is because each of the samples must be presented once per repetition of the acoustic waveform to generate the required secondary wave that the need arises for a frequency multiplier (or divider) 7*a* if only a single synchronising pulse is available from the source, the degree of multiplication is high and depends on the number of samples required and in a typical case this could be 32. The samples stored in the memory 7*c* can be derived in a variety of different ways but since the memory is modified by the unit 13 to minimise the output from the microphone 11, it is not generally too important what the starting samples are, since eventually if each burst of recurring primary sound energy is like each other burst, the correct samples will appear in the memory 7*c* and the pattern of samples one starts with merely affects how long it takes to produce the correct cancelling signal.

Although the foregoing description referred to 32 discrete elements, there could of course be a larger or smaller number. Alternatively, one can interpolate between time elements in such a way as to simulate the effect of a much larger number of elements than are actually present. This interpolation can be performed either in the residual signals line, in order to provide the information for adjusting the appropriate cancelling elements, or can be performed between elements of the cancelling waveform.

Referring again to FIG. 4, the control unit 13 serves to process the residual signal picked up by the residual noise microphone 11, this signal being the sum of the sound from the recurring sound source 1 and the cancelling sound being generated by the transducer 10. In the system described in U.S. Pat. No. 4,153,185, this signal is processed by the control unit 13 to give an output related to the overall power of the residual signal. The cancelling waveform is adjusted so as to reduce this overall power level.

In other words, the adaptor 13 shown in FIG. 1 modifies the waveform memory *7c* to achieve optimum cancellation by first measuring the power in a repeat cycle. This can be achieved by analog means by, for example full wave rectifying the waveform then integrating over, for example, one firing cycle of the engine, or digitally by converting the analog signal to digital form and performing the power calculation in a microprocessor. In the arrangement shown in FIG. 4, the input signal from the residual microphone 11 is fed to an antialiasing filter 13*a*, then to an analog to digital converter 13*b*, next to a power estimator 13*c* and finally to the waveform segment adjuster 13*d*. If the digital approach is adopted, the adaption speed can be increased by employing the technique disclosed in WO81/00638 which instead of working over a cycle can assess the power level in that part of the residual signal which is effected by the waveform segment or segments being modified and can thus apply a correction parameter to that segment in the next repeat cycle. Details of this technique and modifications to it can be found in WO81/00638 (now U.S. Pat. No. 4,417,098).

Since the output from the generator 7 is related in time in an appropriate way with the repetitive bursts of noise from the source 1, very high attenuation of the noise field 2 (e.g. 30 dB or better) is possible, but since the sound 4 is not so synchronised and will have a totally different frequency spectrum from the noise field 2, little attenuation of the sound 4 will normally arise with the active attenuation feedback loop 7, 10, 11, 13, so that the sound 4 passes substantially unaffected into the ear and can now be clearly heard, since the sound field 2 has been greatly reduced in the right ear of the person 3.

If only the right ear is provided with the loop 7, 10, 11, 13, the unit 14 covering the left ear can be a conventional passive ear defender which strongly attenuates both the field 2 and the sound 4. Normally however, better detection of the sound 4 is obtained if the unit 14 is also an open earphone also provided with a feedback loop like the loop 7, 10, 11, 13. The loop 7, 10, 11, 13 can be used for supplying cancelling signals to the left ear, but in practice since the sound field 2 is different in the two ears, better results are obtained with a separate feedback loop for each ear, although the two loops can be synchronized with the same trigger pulses 6.

Figure 2:
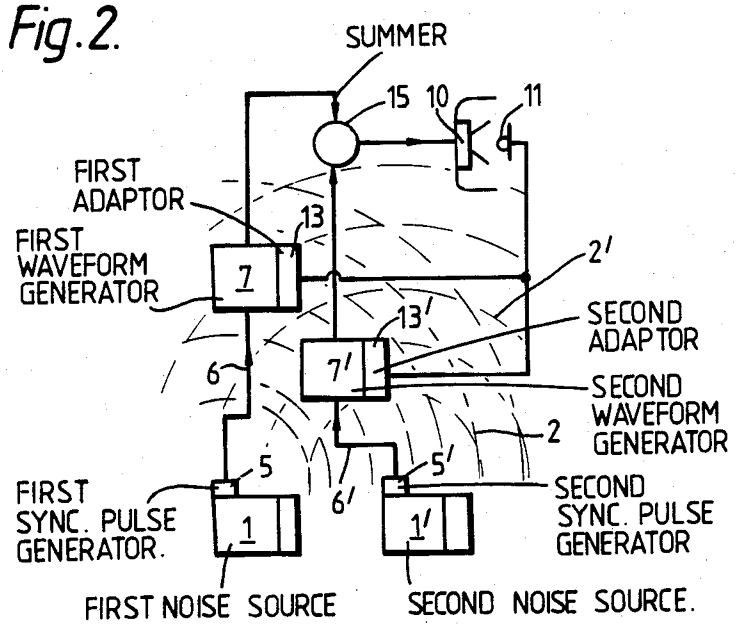
FIG. 2 shows how the system of FIG. 1 can be modified to cancel the noise from two sources of repetitive noise.

FIG. 2 illustrates a similar system to that shown in FIG. 1 and similar reference numerals have been used to designate similar components. In FIG. 2 a second source 1' contributes to the noise field and a second adaptive waveform generator 7' is provided triggered by pulses 6' from the source 1'. The waveforms from the generators 7 and 7' are here shown summed by an electronic summer 15 prior to being fed to the speaker 10 but an alternative method is to employ suitable software in the generator 7 and to connect the generator 7' directly to the generator 7.

In many cases it will be desirable for the person 3 to be mobile and the active ear-defender can then be battery-powered, and mounted, for example, on a headset 8 or carried in a pocket. The synchronisation or triggering pulses 6 can be transmitted to the heat-set in a variety of ways. The synchronisation system used can be common to a number of ear-defenders, e.g. in the case of a passenger-carrying vehicle or, as in the case of engine test cells, the transmission could be sufficiently localised so that the person's receiving unit would "lock on" at the most relevant local synchronisation signal.

In some cases, where the source of noise is particularly regular, it may be possible to generate the source of synchronisation by a phase-locking technique, from the acoustic or vibrational signal sensed in the acoustic or vibration field of the source of repetitive noise.

Modifications of the system shown in FIG. 1 are possible. Many acoustic environments (such as a ship's engine-room) contain repetitive noise in the presence of a significant amplitude of high-frequency noise. This could be attenuated by conventional passive ear-defenders, used in conjunction with the system described herein, or with defenders which produce less pressure on the ears since the seal between the ear-defender and the head (essential for passive attenuation of low frequency) will be much less critical when augmented by an active system which is particularly effective at these lower frequencies. Alternatively, or in addition, a direct feed-back method (c.f. Olsen's original work) could be combined with the system described herein, such that for example, the direct feed-back system attenuates the mid-band frequencies, the passive system operates at the highest audio frequencies, and the "repetitive" system here described operates at the lowest frequencies.

In another arrangement, an acoustic transducer in a headset may be being used to receive electrical signals which contain a desired signal superimposed on a background signal of a repetitive nature. Using the method of the invention, the background signal can be acted on by a cancelling electrical waveform so that the acoustic signal reaching the ear(s) of the headset wearer is substantially only the desired signal.

Figure 3:
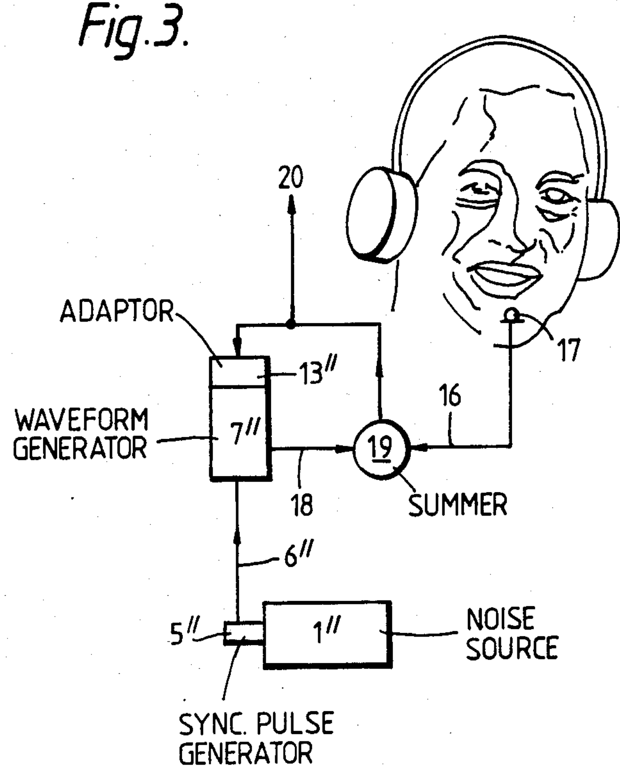
FIG. 3 shows an add-on feature to the apparatus of FIG. 1 for improving speech transmission from a listener in an environment of high background repetitive noise, FIG. 4 gives further details of the apparatus of FIGS. 1 to 3.

FIG. 3 illustrates a further extension of the invention which would improve, for example, clear speech communication over a radio link (e.g. when using the active ear-defender shown in FIG. 1 or FIG. 2). Since the level of speech needed to communicate within, say the cockpit of an aircraft will be lower when the people therein are speaking to one another using the active ear-defenders, than it would be if they were not, the amplitude of the speech will be correspondingly lower, and the radio communication may be impaired because the signal 16 from a microphone 17 would be contaminated by the repetitive noise field. The signal 18 from an adaptive waveform generator 7" would then be added to the microphone signal 16, in a summer 19, the adaptive means 13" being programmed to adapt the generator 7" such that the two summed signals 16 and 18 produce a minimum of those parts of the summed signals which are synchronised to the source 1", but leave any unsynchronised (speech) signal unaffected. The output 20 from the summer 19 would then be fed to a communications system (not shown) for onward transmission.

The cancelling noise need not be generated by a conventional headphone but any transducer capable of producing sufficient power could be used. The transducer could be, for example, a loudspeaker mounted in a headrest or ducted to the vicinity of the head.

We claim:

1. Apparatus for improving the audibility of desired incident sound to a person operating in an environment where there is a substantial background noise in the person's ears coming from a source of repetitive noise, comprising an adaptable waveform generator, head-mounted means including two ear pieces one for each ear of the wearer, each ear piece being equipped with a first electro-acoustic transducer receiving a synthesised cancelling waveform from the generator and generating a cancelling noise adjacent to the respective ear of the person to at least partly null the background noise in that ear, a second electro-acoustic transducer to sense the partially nulled background noise in the person's ear, adaptive means to modify the output of the generator on the basis of the electrical output signal from one of the second transducers to minimize the nulled background noise, the head-mounted means holding the transducers adjacent to the respective ear of the person while allowing said desired incident sound to reach each ear, and means to feed a triggering signal derived from the source to the waveform generator, the apparatus further comprising a third electro-acoustic transducer for picking up the repetitive noise from said source and speech signals from the said person and generating a further electrical output which is characteristic of the noise and speech signals, the further electrical output from said third electro-acoustic transducer being electrically combined with the electrical output from said waveform generator in an opearting means to selectively reduce the effect of the repetitive noise coming from said source on the further electrical output of the third electro-acoustic transducer without significantly affecting the component of said further electrical output which is generated by said speech signals.

2. Apparatus as claimed in claim 1, in which the apparatus is portable and the triggering signal is fed from the source to the apparatus by one of an optical link, an ultra-sonic link and an electrical link.

3. Apparatus as claimed in claim 2, in which there is a separate waveform generator for each first and second transducer.

4. Apparatus as claimed in claim 3, in which the triggering signal is fed to each waveform generator.

5. A method for improving the audibility of desired incident sound to a person operating in an environment where there is a substantial background noise in the person's ears coming from a source of repetitive noise, which method comprises generating an adaptable electrical waveform, feeding the waveform to a respective first electro-acoustic transducer mounted adjacent to each ear of the person to generate a cancelling noise adjacent to the respective ear of the person to at least partly null the background noise in that ear, sensing the partially nulled background noise in each ear with a respective second electro-acoustic transducer, modifying the output of the generator on the basis of the electrical output signal from one of the second transducers to minimize the nulled background noise and allowing said desired incident sound to reach each ear, feeding a triggering signal derived from the source to the waveform generator, the method further comprising using a third electro-acoustic transducer to pick up the repetitive noise from said source and speech signals for the said person and generate a further electrical output which is characteristic of the noise and speech signals, the further electrical output from said third electro-acoustic transducer being electrically combined with the electrical output from said waveform generator to selectively reduce the effect of the repetitive noise coming from said source on the further electrical output of the third electro-acoustic transducer without significantly affecting the component of said further electrical output which is generated by said speech signals.

6. A method as claimed in claim 5, in which the apparatus is portable and the triggering signal is fed from the source to the apparatus by one of an optical link, an ultra-sonic link and an electrical link.

7. A method as claimed in claim 6, in which a separate adaptable waveform is fed to each first transducer and is separately modified by the output from the respective second transducer.

8. A method as claimed in claim 7, in which the triggering signal is fed to each waveform generator.

* * * * *

UNITED STATES PATENT AND TRADEMARK OFFICE

CERTIFICATE OF CORRECTION

PATENT NO. : 4,654,871

DATED : March 31, 1987

INVENTOR(S) : GEORGE B. B. CHAPLIN, RODERICK A. SMITH and TERRENCE P. C. BRAMER

It is certified that error appears in the above-identified patent and that said Letters Patent is hereby corrected as shown below:

Column 1, line 29, "variations" should be --vibrations--.
Column 5, line 64, "heat-set" should be --head-set--.
Claim 1, Column 7, line 12, "each" should be --said--; line 21, "opearting" should be --operating--.

Signed and Sealed this

First Day of September, 1987

Attest:

DONALD J. QUIGG

*Attesting Officer*

*Commissioner of Patents and Trademarks*